(12) United States Patent
Pesis et al.

(10) Patent No.: US 12,622,723 B2
(45) Date of Patent: May 12, 2026

(54) NON-CORING NEEDLE WITH REVERSED SHARP EDGE

(71) Applicant: UPSTREAM PERIPHERAL TECHNOLOGIES LTD., Caesarea (IL)

(72) Inventors: Yossi Pesis, Pardes Hana (IL); Dan Rottenberg, Haifa (IL)

(73) Assignee: Bentley InnoMed GmbH, Hechingen (DE)

( * ) Notice: Subject to any disclaimer, the term of this patent is extended or adjusted under 35 U.S.C. 154(b) by 225 days.

(21) Appl. No.: 18/032,982

(22) PCT Filed: Nov. 8, 2021

(86) PCT No.: PCT/IB2021/060322

§ 371 (c)(1),
(2) Date: Apr. 20, 2023

(87) PCT Pub. No.: WO2022/097111

PCT Pub. Date: May 12, 2022

(65) Prior Publication Data

US 2023/0380858 A1 Nov. 30, 2023

Related U.S. Application Data

(60) Provisional application No. 63/111,153, filed on Nov. 9, 2020.

(51) Int. Cl.
| | |
|---|---|
| *A61B 17/3205* | (2006.01) |
| *A61B 17/22* | (2006.01) |
| *A61B 17/3207* | (2006.01) |
| *A61B 17/34* | (2006.01) |

(52) U.S. Cl.
CPC .... *A61B 17/32053* (2013.01); *A61B 17/3207* (2013.01); *A61B 2017/22038* (2013.01); *A61B 2017/22094* (2013.01); *A61B 2017/3454* (2013.01)

(58) Field of Classification Search
CPC .......... A61B 17/32053; A61B 17/3207; A61B 2017/22038; A61B 2017/22094; A61B 2017/3454
See application file for complete search history.

(56) References Cited

U.S. PATENT DOCUMENTS

| | | | |
|---|---|---|---|
| 2,717,599 | A | 9/1955 | Huber |
| 3,064,651 | A | 11/1962 | Henderson |
| 2003/0069550 | A1 | 4/2003 | Sharp |
| 2009/0259126 | A1 | 10/2009 | Saal |
| 2010/0010413 | A1 | 1/2010 | Loiterman |

FOREIGN PATENT DOCUMENTS

| | | |
|---|---|---|
| DE | 20211110 U1 | 9/2002 |
| WO | WO2020145181 A1 | 7/2020 |

OTHER PUBLICATIONS

PCT Int'l Search Report issued Feb. 2, 2022 in connection with related PCT Appl. No. PCT/IB2021/060322.

*Primary Examiner* — Ashley L Fishback
(74) *Attorney, Agent, or Firm* — Brooks Kushman P.C.

(57) ABSTRACT

A piercing device includes a tube (10) formed with a needle tip (12). The needle tip (12) includes a bevel having a bevel length (BL) that extends at a bevel angle from a base of a heel (14) to a sharp distal, radially outer edge of the needle tip (12). A reversed edge (17) is formed as a reversed edge angle on the heel (14) of the bevel. The bevel angle is an acute angle, and the reversed edge angle is an obtuse angle.

9 Claims, 5 Drawing Sheets

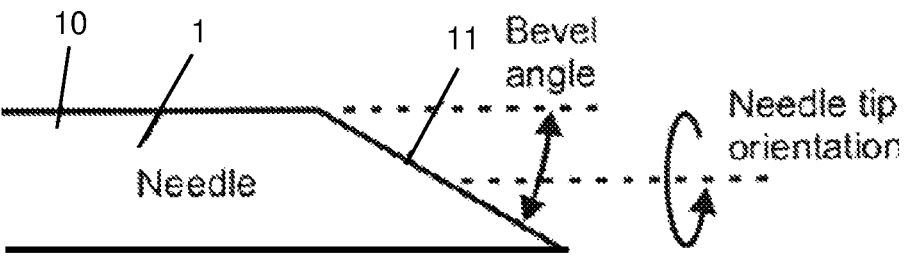
FIG. 1 - PRIOR ART
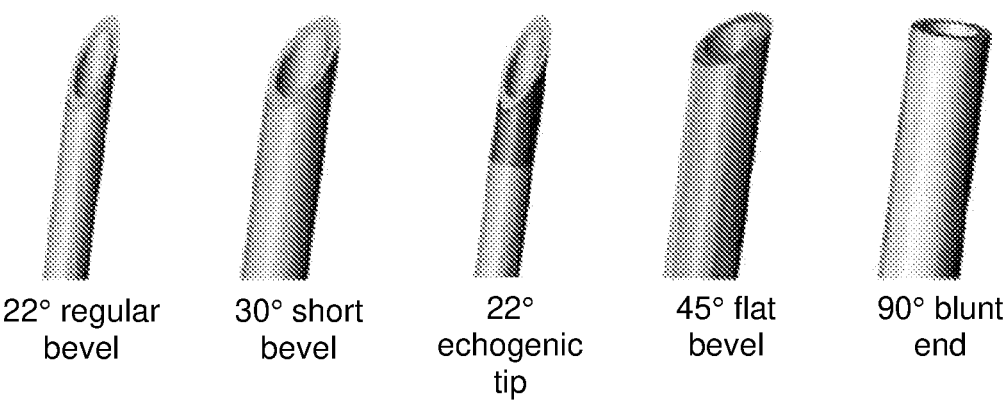
| 22° regular bevel | 30° short bevel | 22° echogenic tip | 45° flat bevel | 90° blunt end |
FIG. 2 - PRIOR ART
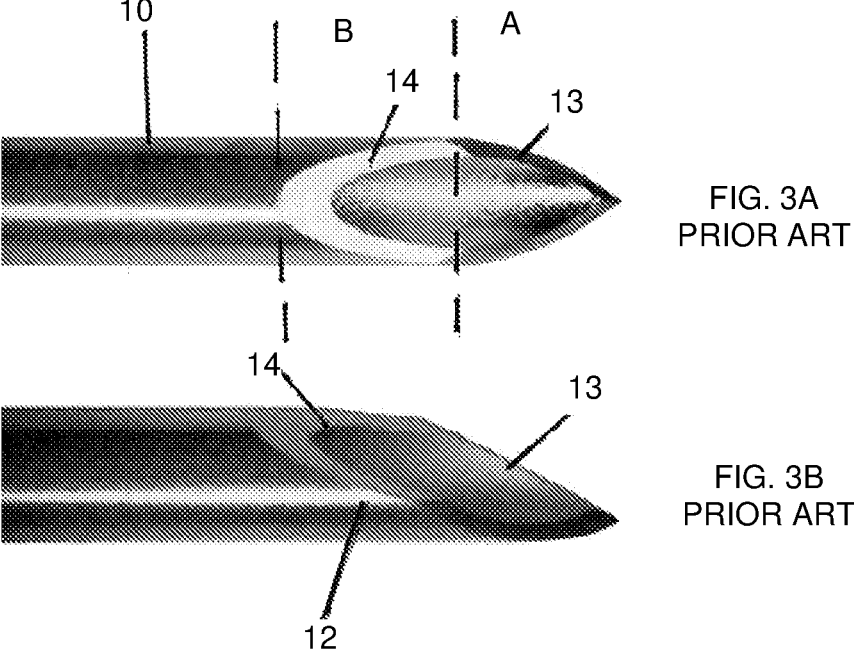
FIG. 3A
PRIOR ART
FIG. 3B
PRIOR ART

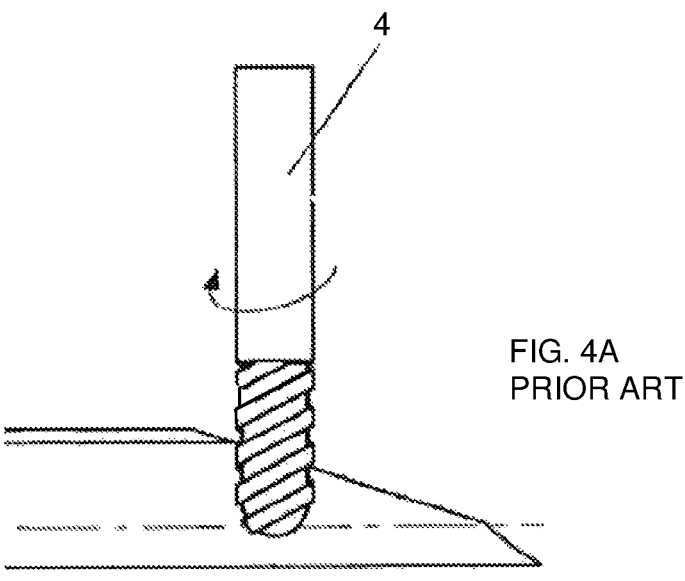
FIG. 4A
PRIOR ART
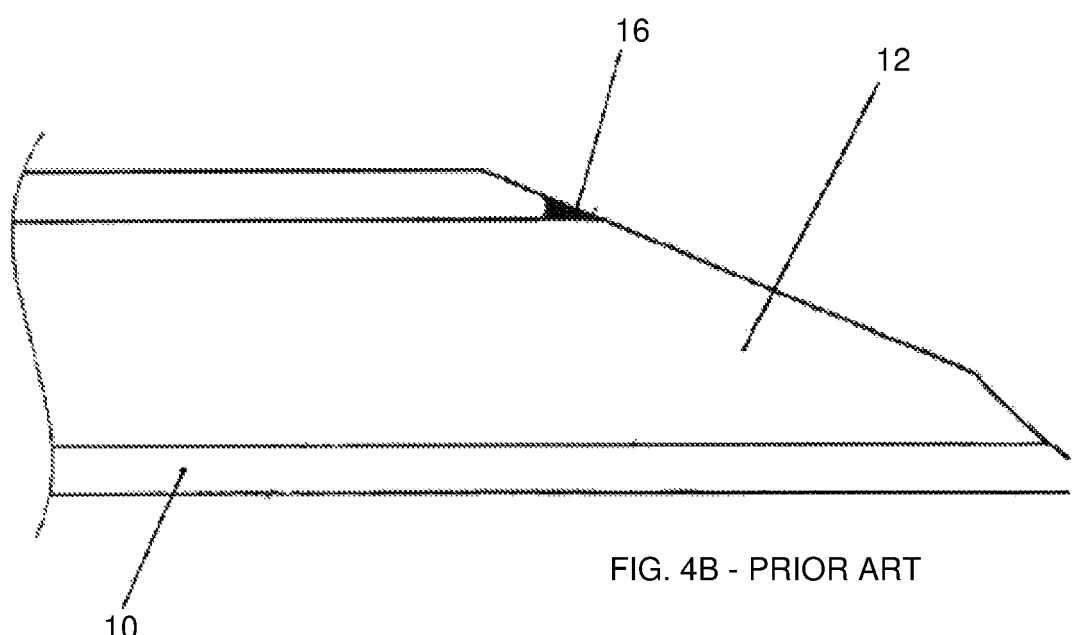
FIG. 4B - PRIOR ART

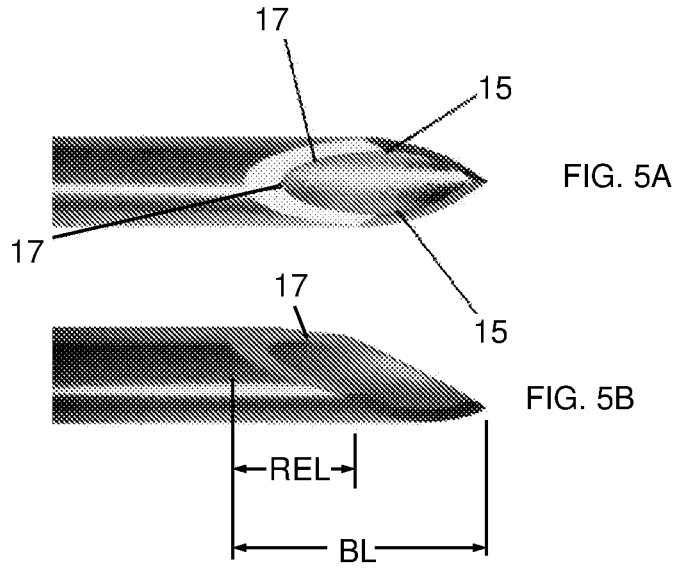
FIG. 5A
FIG. 5B
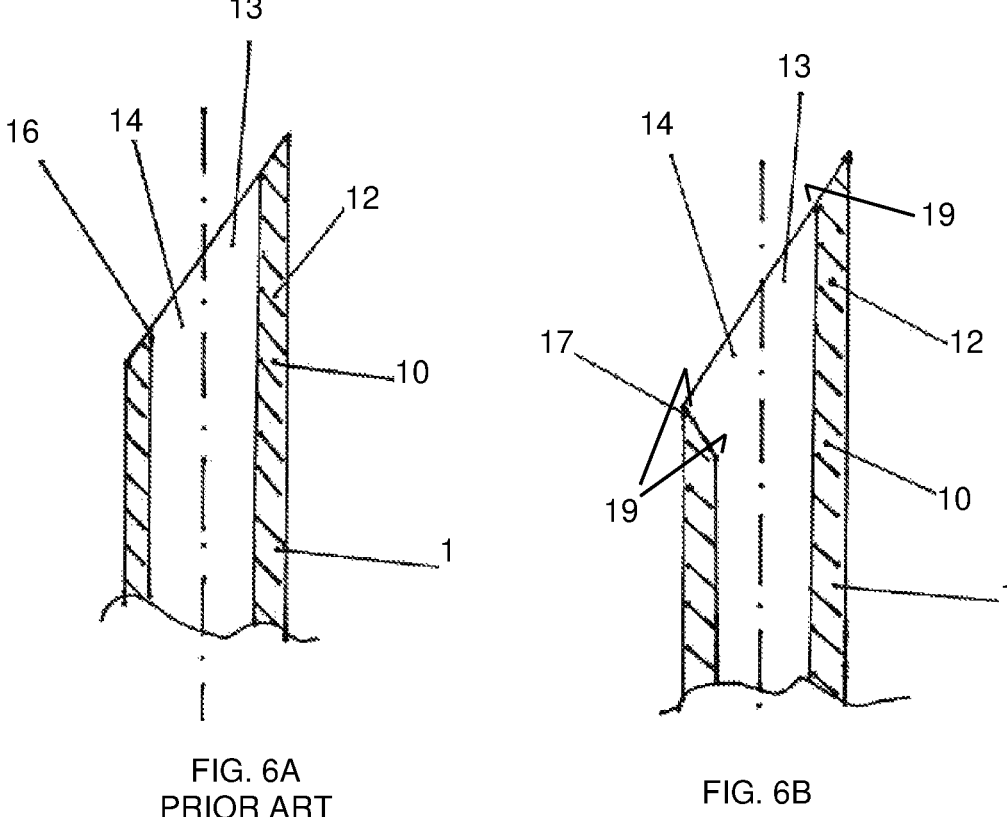
FIG. 6A
PRIOR ART
FIG. 6B

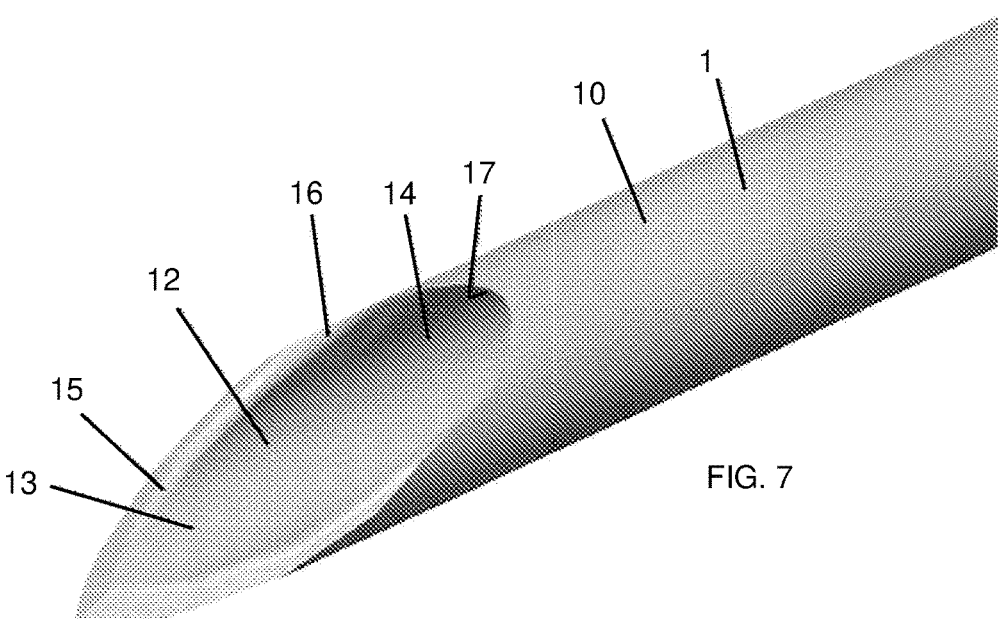
FIG. 7
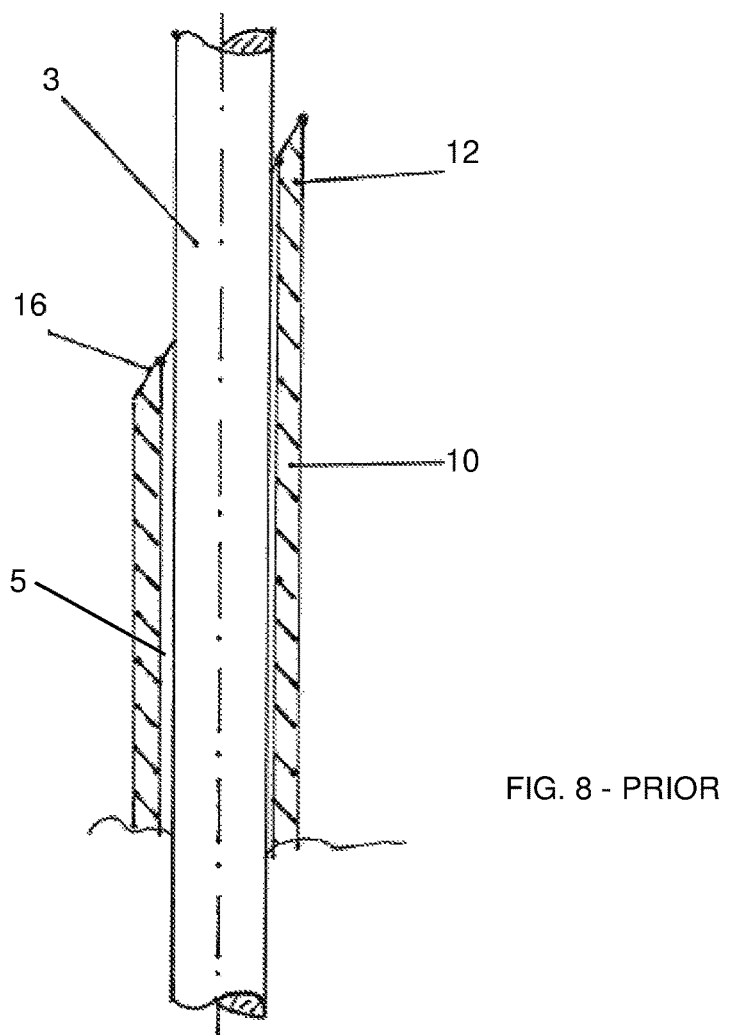
FIG. 8 - PRIOR ART

NON-CORING NEEDLE WITH REVERSED SHARP EDGE

CROSS-REFERENCE TO RELATED APPLICATIONS

This application is the U.S. national phase of PCT Appln. No. PCT/IB2021/060322 filed Nov. 8, 2021, which claims the benefit of U.S. provisional application Ser. No. 63/111, 153 filed Nov. 9, 2020, the disclosures of which are hereby incorporated in their entirety by reference herein.

FIELD OF THE INVENTION

The present invention relates generally to novel needle sharp edges designed to prevent coated guidewires from getting damaged, due to coating abrasion or peeling.

BACKGROUND OF THE INVENTION

Chronic Total Occlusion (CTO) is an arterial vessel blockage (typically of plaque) that obstructs blood flow. CTO can occur both in coronary and peripheral arteries, and generally results from the same underlying cause—athero-sclerosis.

One of the main difficulties in crossing a total occlusion is that the clinician does not know exactly how hard the plaque is until steering a guidewire to the occlusion. If the occlusion is relatively new, the plaque is likely to be soft enough and the guidewire may penetrate the plaque. How-ever, after several weeks or months, the occlusion becomes fibrotic and calcified and the plaque becomes much harder, rendering guidewire crossing of the occlusion difficult if not impossible. Failure to cross the obstruction is the primary failure mode for CTO recanalization.

If the guidewire cannot pass the occlusion, support cath-eters and crossing catheters are used to support the guidewire to pass the occlusion. Such crossing catheters may have a blunt tip.

If CTO intra-luminal crossing is not possible, techniques have been developed for entering the subintimal space and reentering the true lumen after the occlusion. This so-called subintimal recanalization can be a useful procedure and is widely used. One of the advantages of subintimal recanali-zation is that a dissection of the subintimal space is more likely to produce a smooth lumen and improved blood flow than a lumen produced by plowing through calcified plaque. However, technical failure occurs in about 25% of patients undergoing percutaneous subintimal recanalization, mainly due to the inability to reenter the distal true lumen.

If during percutaneous subintimal recanalization, the true lumen cannot be reentered with guidewire manipulation, a true lumen reentry device must be used. Currently there are several specially designed reentry devices in the market. Most of them used straight or curved needle to reenter the guidewire into the true lumen after the occlusion.

Most guidewires available today are polymer coated guidewires, sometimes hydrophilic coated guidewires and many with both polymer and hydrophilic coatings. Such a coating provides significantly less friction and better push-ability. However, using such a coated guidewire with a sharp needle has the risk of damaging the guidewire, when with-drawn backwards, due to abrasion and/or peeling of the coating by the sharp needle edges. This risk is even more severe and dangerous when the guidewire coating abrasion or peeling occurs inside the patient blood vessels.

Some non-coring characteristics can be added to needle tips and are known in the art. Techniques such as gentle mechanical milling of the needle heel, sand-blasting or electro-polish can be used to slightly round the sharp, yet very thin edges of the needle heel. The rounding radius is very small due to the thin wall thickness of the needle hypo-tube. However, in the prior art, only the interior sharp edges of the needle are rounded, and the outer edges remain sharp to penetrate the tissue or plaque. Therefore, in the prior art, masking the outer edges to avoid rounding them is required.

SUMMARY OF THE INVENTION

The present invention seeks to provide novel needle non-coring devices and process thereof. The non-coring needle tip of the present invention allows safe pass of polymer coated guidewires and/or hydrophilic coated guidewires through the sharp needle tip, eliminating the risk of coating abrasion or peeling by the needle sharp edges.

The present invention of non-coring needle tip can be applied on any type of needle tip and any type of catheter, or any other device that includes a sharp needle. The non-coring needle tip of the present invention can be a straight or curved needle tip.

A simple prior art needle is usually made from a metal hypo-tube with bevel cut at an acute angle, usually at about 20°. Sometimes the bevel cut is made with two different angles, called a lancet needle tip.

In the prior art, when pushing a guidewire forward through a device with bevel needle tip at the distal end, the guidewire does not see any sharp needle edges and can pass safely without damage to its coating. Abrasion or peeling of guidewire coating occurs at the back side or the heel side of the needle tip, when the guidewire is pulled back into the device through the needle, meeting very sharp edges of the heel side of the needle tip.

The non-coring needle tip of the invention is based on reversing the direction of the sharp needle edges at the needle heel side. Rounding the needle internal diameter edges can be added to the reversing of the needle heel side sharp edges direction.

In addition, any angle line or edges at the inner needle circumference, even having obtuse angle, at both heel side and needle piercing side, may be rounded to avoid guidewire coating abrasion or peeling.

BRIEF DESCRIPTION OF THE DRAWINGS

The present invention will be understood and appreciated more fully from the following detailed description, taken in conjunction with the drawings in which:

FIG. 1 is an illustration of needle bevel angle of the prior art.

FIG. 2 is an illustration of different bevel angle needles of the prior art.

FIGS. 3A and 3B are illustrations, in two views, of a needle tip with outer and inner cutting edges of the prior art.

FIGS. 4A and 4B are simplified, schematic illustrations of mechanical removal or trimming of the sharp heel base of a needle of the prior art.

FIGS. 5A and 5B are illustrations, in two views, of the needle tip acute and obtuse angle lines to be rounded in an embodiment of the present invention.

FIG. 6a is a schematic cross-section illustration of stan-dard needle tip of the prior art.

FIG. 6b is a schematic cross-section illustration of the needle tip, in an embodiment of the invention, with the needle heel sharp edges reversed direction.

FIG. 7 is a schematic view illustration of the needle tip of the invention with heel side angle reversed back, and both internal heel side and needle piercing side are rounded.

FIG. 8 is a schematic cross-section illustration of prior art needle tip and polymer coated guidewire inside the needle.

DETAILED DESCRIPTION

Figure 9:
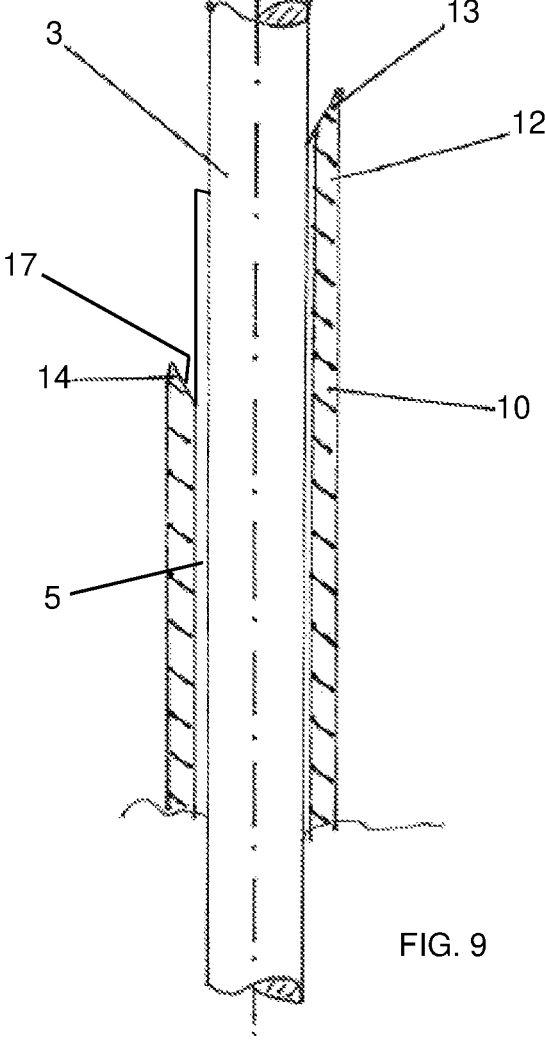
FIG. 9 is a schematic cross-section illustration of the needle tip of the invention and polymer coated guidewire inside the needle.

A simple needle 1 of the prior art, shown in FIG. 1, is usually made from a metal hypo-tube 10 with a bevel cut 11 at an acute angle. The bevel angle can vary as shown in FIG. 2, but most regular needles have acute angle of 15-30°. Sometimes the bevel cut is made with two different angles, called a lancet needle tip.

Reference is now made to FIGS. 3A and 3B, which illustrate a standard bevel needle tip 12 of the prior art. The tip can be divided into area A, which is the piercing section 13 of the needle tip, and area B, which is the heel side 14 of the needle tip.

Piercing section 13 occupies about 180° of the needle tip 12 front section, while heel section 14 occupies the other more proximal 180° section of the needle tip 12. The outer circumference angles of piercing section 13 are acute angles designed to cut through tissue or plaque, while the inner circumference angles of the piercing section 13 are obtuse angles. The outer circumference angles of heel section 14 are obtuse angles while the inner circumference angles of the heel section 14 are acute angles.

When pushing a guidewire forward through a device or hypo-tube 10 of a device with bevel needle tip 12 at the distal end, the guidewire does not encounter any sharp needle edges and can pass forward safely without damage to its coating. Abrasion or peeling of guidewire coating occurs at the back side or the heel side 14 of the needle tip, when the guidewire is pulled back into the device through the needle, meeting very sharp edges of the needle tip heel side while withdrawn.

In the prior art, if needle tip 12 includes non-coring, such non coring is based on trimming the inner circumference 16 of the heel section 14 using different methods, including using mechanical milling tool 4 [FIG. 4], or electro-polish or sand blasting on the specific heel area.

Reference is now made to FIGS. 5A-5B. In an embodiment of the non-coring needle tip 12 of the present invention, the needle non-coring is based not on rounding, or not just on rounding, any internal sharp edge of the needle heel section 14, but by reversing the direction of the sharp needle edges 17 at the needle heel side. Rounding the needle heel internal diameter edges can be added to the reversing of the needle heel side sharp edges direction. In other words, the bevel angle of the needle tip is an acute angle, whereas the reversed edge angle of reversed edge 17 is an obtuse angle.

Reference is now made to FIG. 6A, which illustrates a standard prior-art needle cross-section, in which edges 16 of heel 14 are formed as an acute angle pointing inward.

Reference is now made to FIG. 6B, which illustrates a cross-section view of needle tip 12 of a tube 10 of an embodiment of the invention. Sharp edges 17 of the heel section 14 have a reversed direction in which they point outward. Because sharp edges 17 point radially outwards, any guidewire passing through the needle tip 12 will not encounter any acute angle, both in the forward and backward directions.

The reversed edge 17 may have an acute angle of 15-45° relative to the outer surface of tube 10, that is, the reversed edge angle is an obtuse angle of 105-135°; alternatively, an obtuse angle of 105-130°; alternatively, an obtuse angle of 105-125°; alternatively, an obtuse angle of 105-120°; alternatively, an obtuse angle of 105-115°; alternatively, an obtuse angle of 105-110°; alternatively, an obtuse angle of 100-135°; alternatively, an obtuse angle of 100-130°; alternatively, an obtuse angle of 100-125°; alternatively, an obtuse angle of 100-120°; alternatively, an obtuse angle of 100-115°; alternatively, an obtuse angle of 100-110°.

Reference is now made to FIG. 5A. The bevel extends from the base of the heel to the needle tip and has a length BL. The reversed edge 17 has a length REL which may be from the beginning of the heel, which is at the base of the bevel of the needle tip, up to half the bevel length BL; alternatively, the length of reversed edge 17 may be less than half the bevel length BL; alternatively, the length of reversed edge 17 may be more than half the bevel length BL; alternatively, the length of reversed edge 17 may be less than half the bevel length BL and more than a third of the bevel length BL.

The needle of the invention may be manufactured with the reversed edge 17 by any suitable manufacturing process. The invention can also be carried out by modifying an existing needle to form the reversed edge 17. For example, in order to reverse the direction of the prior art heel section edge 16, first there is a need to remove, using a mechanical tool or by any other means, the sharp edges 16 to get about the straight wall at the heel section 14, and then start reversing the angle direction using small mechanical milling or grinding tools or any other metal removing method known in the art. By doing this procedure, the shape of the needle tip 12 heel section changes and the needle tip opening length is increased, as can be seen in FIG. 7.

In another embodiment of the present invention, any angle line or edges at the inner needle surface, including even the obtuse angle, at both heel side and needle piercing side, are rounded to form rounded edges 19 to avoid guidewire coating abrasion or peeling, as seen in FIG. 6B. The radius of rounded edges 19 may be, without limitation, in the range of 0.1-0.5 mm.

Reference is now made to FIG. 8. A guidewire 3 has a polymer coating 5 and is inserted in a prior art needle. The polymer coating 5 can get abraded and peeled by the sharp edge 16 of the needle. In contrast with the prior art, in an embodiment of the invention as shown in FIG. 9, the polymer coating 5 of the guidewire 3 is not abraded at all by the reversed edge 17.

What is claimed is:

1. A piercing device comprising:

a tube (10) formed with a needle tip (12), said needle tip (12) comprising a bevel having a bevel length (BL) that extends at a bevel angle from a base of a heel (14) of the bevel to a sharp distal, radially outer edge of said needle tip (12); and a reversed edge (17) including a planar surface on the heel (14) of the bevel and rounded edges (19) at both an internal heel side of the bevel and an internal needle piercing side of the bevel, wherein a reversed edge angle between an outer surface of the tube at the heel side of the bevel and the planar surface is an obtuse angle.

2. The piercing device according to claim 1, wherein said reversed edge angle is an obtuse angle of 100-135°.

3. The piercing device according to claim 1, wherein said reversed edge angle is an obtuse angle of 100-130°.

4. The piercing device according to claim 1, wherein said reversed edge angle is an obtuse angle of 100-125°.

5. The piercing device according to claim 1, wherein said reversed edge angle is an obtuse angle of 100-120°.

6. The piercing device according to claim 1, wherein said reversed edge angle is an obtuse angle of 100-115°.

7. The piercing device according to claim 1, wherein said reversed edge angle is an obtuse angle of 100-110°.

8. The piercing device according to claim 1, wherein said bevel has a bevel length and said reversed edge (17) has a length up to half the bevel length.

9. The piercing device according to claim 1, wherein said bevel has a bevel length and said reversed edge (17) has a length more than half the bevel length.

\* \* \* \* \*